(12) United States Patent
Howieson et al.

(10) Patent No.: US 6,225,593 B1
(45) Date of Patent: May 1, 2001

(54) MEDICAL APPARATUS FOR GENERATING AN IONISED GAS PLASMA FLAME

(75) Inventors: Maurice Howieson, Edinburgh; Peter John Cain, Midlothian, both of (GB)

(73) Assignee: Helica Instruments Limited, Edinburgh (GB)

( * ) Notice: Subject to any disclaimer, the term of this patent is extended or adjusted under 35 U.S.C. 154(b) by 0 days.

(21) Appl. No.: 09/367,386

(22) PCT Filed: Feb. 13, 1998

(86) PCT No.: PCT/GB98/00327

§ 371 Date: Dec. 13, 1999

§ 102(e) Date: Dec. 13, 1999

(87) PCT Pub. No.: WO98/35618

PCT Pub. Date: Aug. 20, 1998

(30) Foreign Application Priority Data

Feb. 15, 1997 (GB) .................................................. 9703159

(51) Int. Cl.[7] .................................................. B23K 10/00
(52) U.S. Cl. .............................. 219/121.57; 219/121.54; 315/111.21; 606/29; 606/30; 606/32
(58) Field of Search ..................... 219/121.57, 121.52, 219/121.48, 121.54; 315/111.51, 111.21; 606/27–32

(56) References Cited

U.S. PATENT DOCUMENTS

| 5,086,205 | * | 2/1992 | Thommes | 219/121.54 |
| 5,376,768 | * | 12/1994 | Pasquini et al. | 219/121.57 |
| 5,747,935 | * | 5/1998 | Porter et al. | 315/111.51 |

FOREIGN PATENT DOCUMENTS

| 0353178 | * | 1/1990 | (EP) . |
| 95/26686 | * | 10/1995 | (WO) . |

* cited by examiner

*Primary Examiner*—Mark Paschall
(74) *Attorney, Agent, or Firm*—Fleshner & Kim, LLP

(57) ABSTRACT

Apparatus (10) for generating an ionized gas plasma flame for use in medicine, particularly for cauterization, is described. The apparatus (10) has an electrical power source (12) providing an alternating voltage at a fixed frequency and a resonant circuit (16, 26) resonant at the fixed frequency connected to the electrical power source (12). A single insulated electrical conductor (30) is connected to the output (18) of the reactive circuit (16) and terminates at a nozzle (36). Conduit means (32) surrounds the electrical conductor (30) along its length and defines a gas-flow channel for supplying substantially inert gas to the nozzle (36), where the gas-flow emerges as a plasma.

17 Claims, 3 Drawing Sheets

MEDICAL APPARATUS FOR GENERATING AN IONISED GAS PLASMA FLAME

This invention relates to apparatus for generating an ionised gas plasma flame for use in medicine, particularly for cauterisation. A known form of apparatus for generating an ionised gas plasma flame for use in cauterisation is disclosed in WO 95/26686 and provides a corona-type flame issuing from a nozzle. The corona flame has a high electron temperature but a low molecular temperature, typically about 20° C. When the nozzle is brought close to (within 5 mm of) a surface that is connected to electrical earth, either directly or by stray capacitance, the corona-type flame changes to an arc-discharge flame (which has a high molecular temperature typically of the order of 800° C). The flame takes place in the plasma provided by the flowing gas which, being inert, minimises oxidation occurring at the earthed surface.

Accordingly, when the surface is part of a human or animal body the plasma can be used to stop flow of blood from damaged tissue by cauterisation. Alternatively, the heat from the arc-discharge flame can be used to remove layers of tissue.

Some surgical techniques require very low operating powers, for example less than 50 W. However, the prior art cauterising apparatus requires complex control methods to produce operating powers of less than 50 W. Typically, these complex control methods apply variable-length bursts of radio-frequency (in the region of 1 MHz) energy to the plasma.

Operating at power levels of less than 5 W requires special consideration because the voltage required to initiate a discharge at these low operating powers (5 W) is the same as the voltage required to initiate a discharge at higher operating powers (greater than 150 W). However, using a high voltage increases the power supplied to the plasma. The prior art apparatus uses a high output-impedance circuit to limit current flow when operating at power levels below 5 W, however, these high output-impedance circuits are very complex.

It is an object of the present invention to provide an improved circuit for controlling cauterising apparatus at low powers.

According to a first aspect of the present invention there is provided apparatus for generating an ionised gas plasma flame for use in medicine, particularly for cauterisation, comprising:

an electrical power source providing an alternating voltage at a fixed frequency in the Kilohertz region and with a magnitude below 100 V, a resonant circuit approximately resonant at the fixed frequency connected to the electrical power source, a single insulated electrical conductor leading from the output of the resonant circuit and terminating with an insulation-free tip, conduit means surrounding the electrical conductor along at least part of its length for delivering a supply of substantially inert gas to the insulation-free tip, an end piece terminating the conduit means and surrounding the insulation-free tip of the conductor, wherein the end-piece at its free end defines a nozzle through which the gas-flow can emerge, whereby the resonant circuit includes an in-series inductance to limit plasma current flow and the resonant circuit provides a magnified voltage so that the gas-flow may be ionised to form a plasma by the magnified voltage supplied to the tip.

By virtue of the present invention, a low voltage fixed frequency power supply may be used to initiate and maintain a low power plasma discharge. This is achieved by using a reactive circuit that is resonant at this fixed frequency so that when the plasma is formed the voltage is reduced because of the impedance provided by the plasma relative to the resonant circuit, thereby reducing the current flow and the power delivered to the plasma.

Preferably, a step-up transformer is used to increase the voltage from the power source.

Preferably the power source operates at a fixed frequency in the range 30–90 KHz and at a voltage in the range 2–50 V with a power level less than 30 watts.

Preferably, the gas has a low breakdown potential, suitable gases include He, Ar, Ne, $H_2$ or $N_2$ or a combination thereof. The gas may additionally include a small amount (e.g. less than 25%) of $O_2$.

Preferably, a voltage detector continuously monitors the voltage at the tip so that the amplitude of the output voltage from the power source is reduced when the voltage at the tip is above a predetermined value.

According to a second aspect of the present invention there is provided a method of controlling cauterising apparatus, where the method comprises the steps of measuring the capacitance of a reactive element in the cauterising apparatus, selecting a fixed frequency in the kilohertz region for a sinusoidal generator which provides an alternating voltage at the said fixed frequency, the alternating voltage having a magnitude less than 100 V, and selecting a value of a resonating reactive element such that the reactive element and said resonating reactive element are approximately at resonance at the said fixed frequency, so that voltage magnification is provided whereby the voltage has sufficient amplitude to initiate and maintain a plasma discharge.

It will be understood that the reactive element may be implemented by parasitic effects such as stray capacitance. It will also be understood that the term "at resonance" refers to the circuit being sufficiently close to resonance for voltage magnification effects to be important.

Preferably, the method includes the step of using a resistive element to limit the voltage magnification produced by the reactive element and the resonating reactive element.

An embodiment of the present invention will now be described by way of example with reference to the accompanying drawings; in which.

Figure 1:
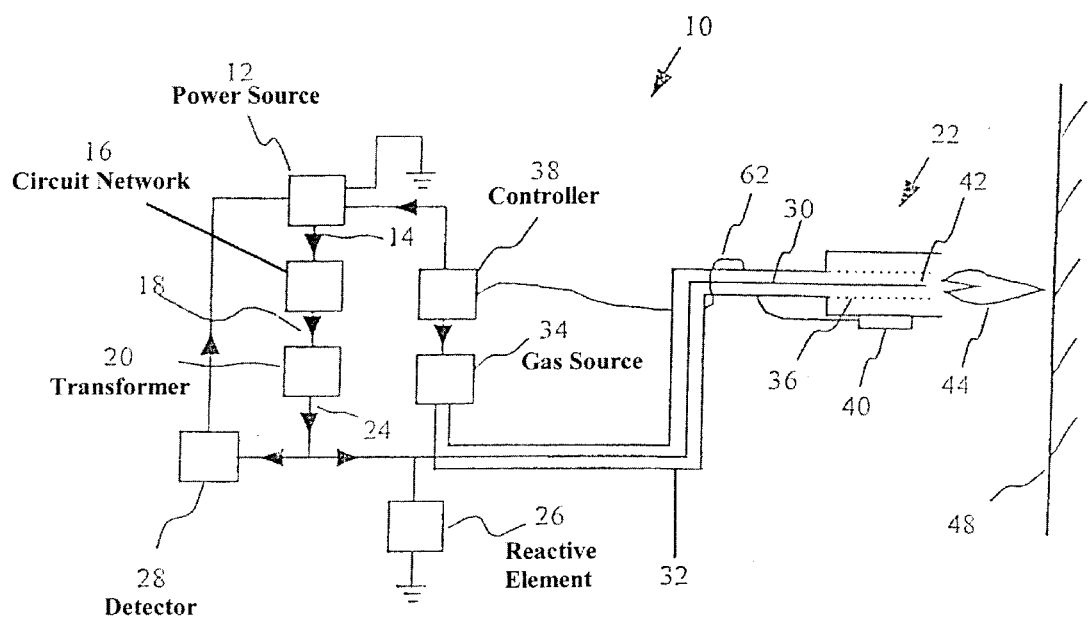
FIG. 1 is a block diagram of apparatus according to one embodiment of the present invention.

The cauterising apparatus 10 shown in FIG. 1 comprises an electrical power source 12, in the form of a sinusoidal generator, which is capable of providing at its output 14 an alternating (sine wave) voltage at a fixed frequency (f1) in the low kilohertz region and with a magnitude less than 100 V with respect to earth, typically 5 V for low power (5 W) operation. In this embodiment, the fixed frequency (f1) is selected to be 50 kHz.

The output 14 of the sinusoidal generator 12 is connected to a circuit network 16 (the function of which will be explained) having an output 18 connected to a step-up transformer 20 with a turns ration of 30 to 1. The transformer 20 increases the voltage from the circuit network output 18 to provide sufficient working voltage for a probe 22 having an insulated wire 30 connected to the transformer output 24. The wire 30 is effectively coupled to earth capacitively due to parasitic effects and this is represented by a reactive element 26. The reactive element 26 also represents capacitive coupling to earth of the transformer windings. A detector 28 is connected to the output of the transformer 20 and will be described in more detail below.

A conduit 32 surrounds a portion of the length of the wire 30, i.e. the wire 30 is completely surrounded by conduit 32 for some of its length. This conduit 32 is electrically non-conducting and defines a gas-flow channel exteriorly of the wire 30. A gas source 34 is used to supply the conduit 32 at its end adjacent the transformer 20 with a substantially inert gas, in this embodiment helium. The gas pressure used is typically 1.5 psi. This low pressure (1.5 psi) has the advantage of reducing the amount of gas that is injected into the bloodstream compared with cauterising apparatus that uses higher pressures of gas. The other end of the conduit 32 is formed into a tubular end piece 36 inside the probe 22.

To regulate and control the apparatus 10 a controller 38 is provided, the outputs of which control the sinusoidal generator 12 and the gas source 34 as will be explained below. The controller 38 is responsive to a manually-controlled actuator device 40 attached to the probe 22 to allow easy operator adjustment of the gas flow and the electrical power.

The probe 22 enables helium gas from the gas source 34 which flows through the conduit 32 to issue from the end piece 36. Within the end-piece 36, the insulated wire 30 has an insulation-free tip 42, which, when electrically energised, causes the issue of helium to become a self-ignited ionised plasma flame 44 (i.e. "strikes" the plasma). The plasma, when brought close to tissue 48, can be used to cauterise the tissue 48 because of the high molecular temperature (800° C.).

The detector 28 is connected in a feedback circuit which is used to control the amplitude of the voltage output from the sinusoidal generator 12. The detector 28 continuously monitors the voltage at the transformer output 24. If the voltage at the transformer output 24 exceeds a predetermined value (for example 1200V) then the detector 28 automatically reduces the amplitude of the output voltage from the sinusoidal generator 12 to reduce the voltage at the transformer output 24 to the predetermined value.

Figure 2:
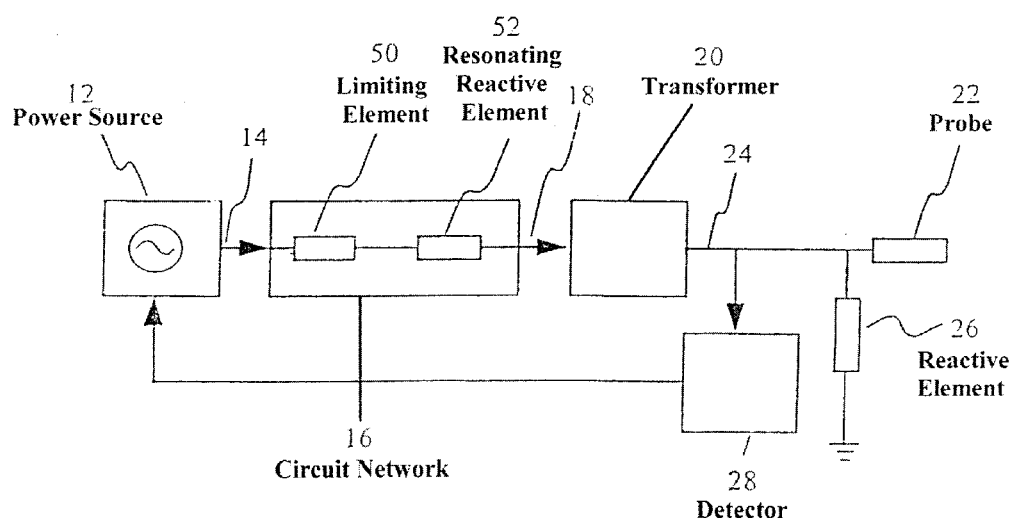
FIG. 2 is a block diagram of some of the electrical components of FIG. 1.

FIG. 2 shows a block diagram of some of the electrical components of FIG. 1, in particular, the circuit network 16.

The circuit network 16 has a limiting element 50 and a resonating reactive element 52 in the form of an inductor, the value of which is selected in relation to that of the reactive element 26 to achieve resonance at the chosen fixed frequency f1 of the generator 12. The voltage magnification that results from resonance, although limited by element 50, means that a relatively low sinusoidal generator output voltage will be sufficient (once magnified by the circuit 16 and stepped-up by transformer 20) to initiate a discharge at the probe 22.

In this embodiment the sinusoidal generator 12 generates an alternating voltage with a frequency of 50 kHz. The reactive element 26 typically has a (measured) capacitance value of approximately 100 pF.

The standard equation for determining the resonant frequency of an electrical circuit is given in equation 1 below.

$$\text{Resonant Frequency (hz)} = \frac{1}{2\pi\sqrt{LC_N}} \quad (1)$$

where $C_N$ in this embodiment is equal to the value of reactive element 26 multiplied by the square of the ratio of transformer turns, i.e. 100 pF multiplied by $30^2$, which equals 0.09 μF; and L is the value of the resonating reactive element 52, which is an inductor. Thus, typically, equation 1 yields a value of 113 μH for the resonating reactive element 52. However, the value of the reactive element 26 is not known exactly, so the value of resonating reactive element 52 is simply selected as 100 μH to ensure that the circuit network 16 is approximately at resonance for the frequency of 50 kHz.

The limiting element 50 (sometimes known as a Q-spoiling resistor) determines the quality factor of the resonant circuit. The limiting element 50 is added to reduce the sharpness of the resonant peak; that is, to limit the voltage magnification produced by the resonant circuit comprising reactive element 26, and resonating reactive element 52. The limiting element 50 is used because the detector 28 may not be able to respond quickly enough to transient changes in the plasma or when the sinusoidal generator 12 is energised. The detector 28 is used in addition to the limiting element 50 so that the value of the limiting element 50 is not critical.

The reason that the voltage magnification produced by the resonant circuit 16 may need to be limited is that there can be voltage breakdown problems in the transformer 20 and particularly in the secondary circuit of the transformer if the input voltage to the transformer is too high (for example, greater than approximately 2 kV).

The value of the limiting element 50 is therefore selected to ensure that there is sufficient magnification of the output signal 14 to initiate a discharge, but not so much magnification that breakdown problems occur.

In practice, the value of limiting element 50 may be selected to ensure that ionisation of the gas flow occurs at distances between two and four times larger than the normal working distance between the probe 22 and the tissue 48 to be cauterised, which typically is less than 5 mm. This ensures that as the probe 22 is brought towards the tissue 48 the ionised plasma flame 44 is produced (the cauterising discharge commences).

The controller 38 is influenced by actuator 40 which can be situated locally to controller 38 but in this embodiment is situated locally to the probe 22. In particular, actuator 40 may take the form of an optical fibre switch arrangement as shown in either of FIGS. 3A and 3B. In both cases interrogation light from the controller 38 is delivered to the switch unit 40 via one or more optical fibres 62 extending along the outer surface of the conduit 32 in any geometric configuration (shown helically wound in FIG. 1 in the interests of clarity). The interrogation light returned to the controller 38 is proportional to the force F applied to the switch and is quantified and the controller 38 provides its outputs accordingly.

Figure 3A:
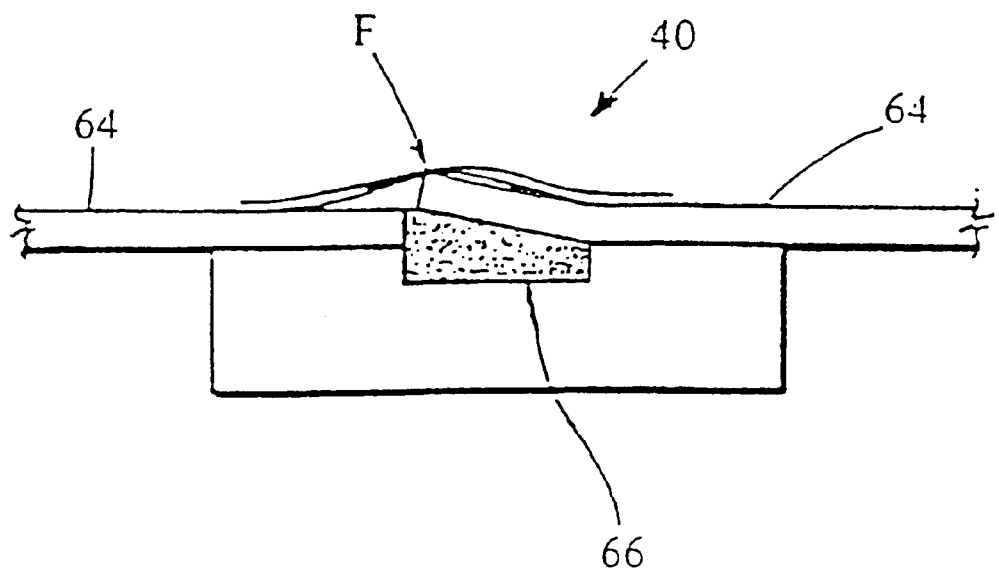
FIGS. 3A and 3B illustrate alternative forms of a detail in FIG. 1.
Figure 3B:
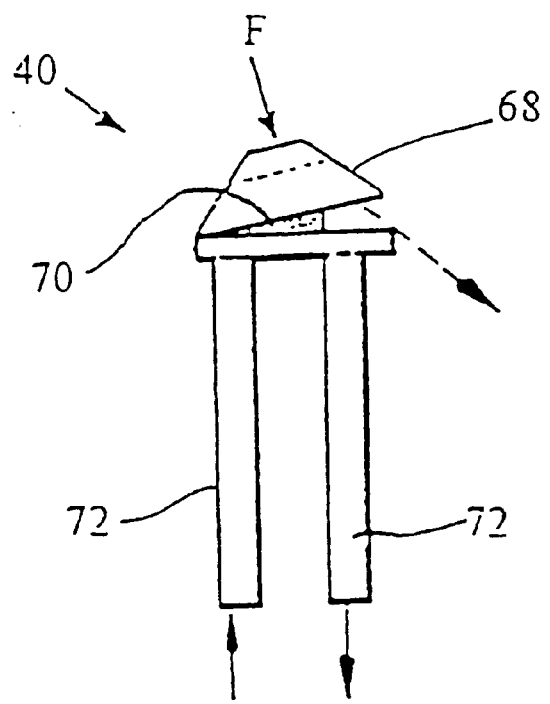

In FIG. 3A the switch 40 is formed by a break in a length of optical fibre 64 with one portion of the fibre 64 being mounted on a resilient pad 66 so as to be manually movable into and out of alignment with the other portion of the fibre 64. In FIG. 3B the switch 40 is formed by a prism 68 mounted resiliently on a pad 70 adjacent to the ends of two fibres 72 and manually movable so as to bring the two fibres 72 into and out of optical continuity. Both switch arrangements described provide a gradual or incremental response so that controller 38 can gradually or incrementally vary the supplies 12,34.

Figures 4A, 4B:
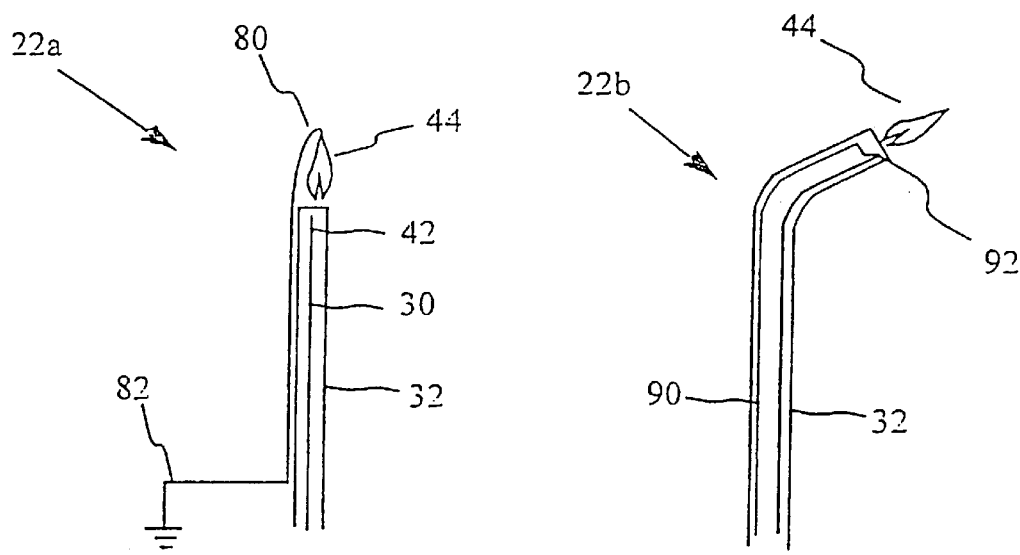
FIGS. 4A and 4B illustrate alternative forms of another detail of FIG. 1.

FIGS. 4A and 4B illustrate alternative forms of the probe 22 of FIG. 1. In FIG. 4A, the probe 22a has a curved blade 80 at the end of the conduit 32. The blade 80 has a pointed end and is connected to electrical earth by earth wire 82. This shape of probe 22a ensures that the plasma flame 44 issues between the end of the blade 80 and the tip 42 of wire 30. Thus, using probe 22a, cutting and cauterising can take place simultaneously because the pointed end of blade 80 becomes heated. This is useful in laparoscopic and endoscopic procedures.

In FIG. 4B, the probe 22b is angled partway along its length for ease of use in certain cauterising operations, such as those performed on the back portion of a nose. The end portion of the conduit 32 is angled at approximately 45 degrees. There is a copper tube 90 (which is a tubular form of wire 30) extending the length of the conduit 32 and which is also angled at approximately 45 degrees. The tube 90 has a pointed end 92 from which the discharge initiates.

Many different control regimes are possible but it is preferred that at initial switch-on the gas supply 34 is given a high flow rate for a short period of time to purge the conduit 32 of air and thereafter the gas supply 34 delivers at a constant flow rate of 2–6 liters/minute.

Figure 5:
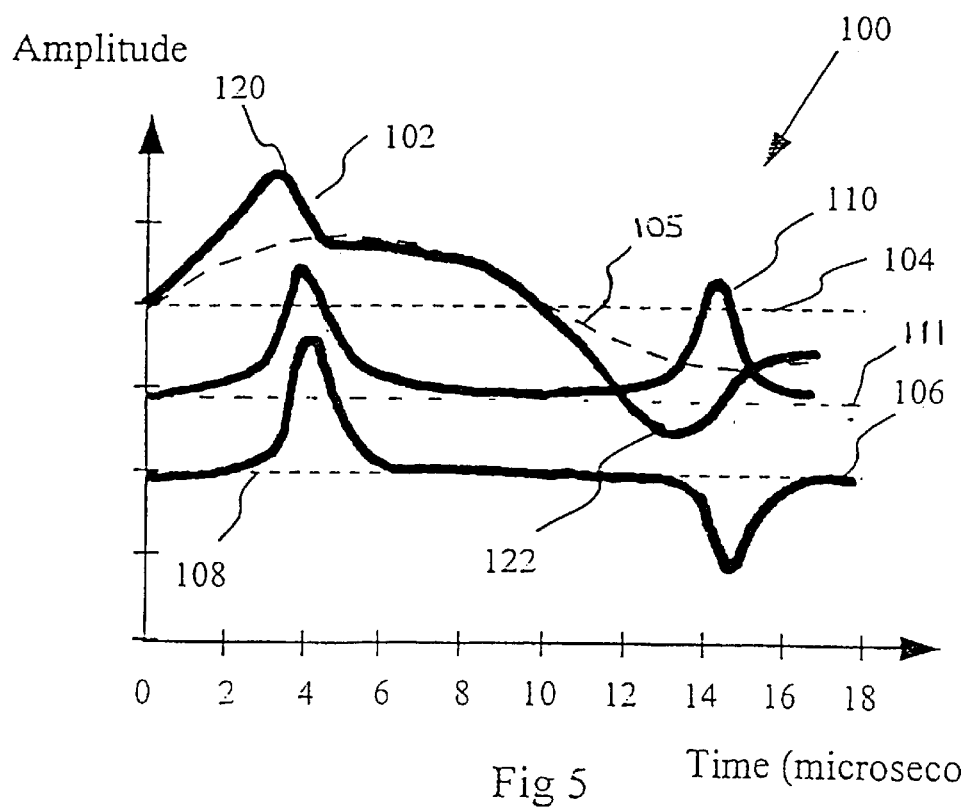
FIG. 5 is a graph of the variation with time of certain electrical parameters when the apparatus of FIG. 1 is in use.

FIG. 5 is a graph 100 illustrating the variation with time of three electrical parameters (voltage, current, and power) when the apparatus of FIG. 1 is in use. The x-axis of the graph 100 is time in microseconds, 20 _seconds represents one period for a 50 kHz signal; the y-axis is amplitude, the scale is unmarked because the units are different for each of the three parameters.

The voltage at tip 42 is shown by line 102 relative to a zero voltage line 104. The peak voltage on line 102 is approximately 800 V. The voltage output from the sinusoidal generator 12 is shown by line 105, the amplitude scale for line 105 is not the same as for line 102, the peak voltage for line 105 is approximately 5 V, compared with 800 V for line 102. The current flowing in the plasma in response to the voltage at tip 42 is shown by line 106; line 106 being relative to a zero ampere line 108. The power delivered to the plasma (the product of the voltage and the current) is shown by line 110 relative to the zero watt line 111.

When a voltage is applied to the tip 42 prior to initiation of the plasma discharge, the resonant circuit (comprising circuit 16 and reactive element 26) causes voltage magnification until the (stepped-up) voltage reaches a level capable of initiating the plasma discharge, shown on line 102 as point 120, then the plasma is formed. On formation of the plasma, a reduced but large impedance is presented by the plasma and the stepped-up magnified voltage (the tip voltage) 102 falls to a level below that required to initiate the discharge because there is now voltage drop across the resonant circuit and across the plasma. Thus, the voltage magnification effect is most noticeable prior to initiation of the plasma discharge.

As shown by line 106, prior to formation of the plasma negligible current flows. On formation of the plasma a large current flows (limited by resistive element 50 and the inductor 52), shown by line 106, until the tip voltage decreases below a threshold level.

The tip voltage decreases as the power supply voltage decreases until the tip voltage reaches a negative (threshold) level sufficient to cause current to flow in the plasma; at this point 122 current again flows until the tip voltage rises above the threshold for current flow.

Thus, current flows in the plasma when the magnitude of the tip voltage exceeds a threshold level, thereby imparting energy to the plasma discharge. The plasma has sufficient energy to sustain itself between these current flow cycles.

It will be apparent that the total power delivered to the plasma is very low (as shown by line 110 because current only flows for a short period of time when the magnitude of the tip voltage is above a certain threshold level. This has the advantage that the cauterising apparatus can initiate and maintain a plasma while delivering only low power levels to the plasma. As a consequence, delicate cauterisation procedures can be performed.

It will be appreciated that various modifications may be made to the above embodiment within the scope of the present invention. For example, in other embodiments the electrical power source produces a voltage with a square or a triangular waveform.

In other embodiments of the present invention the gas used is a gas with a low breakdown potential such as hydrogen ($H_2$), argon (Ar), neon (Ne), nitrogen ($N_2$) or a combination of these. The gas used may also include a small amount (less than 25%) of oxygen ($O_2$).

In the embodiment described, the resonating reactive element 52 is selected to be approximately in resonance with the reactive element 26. It will however be understood that, the resonating reactive element 52 may comprise a plurality of differently-valued reactive elements (such as three inductors, each having a different value), each of which is selectable by a switch. The differently-valued reactive elements may be used to ensure that the resonant frequency of the circuit network 16 comprising limiting element 50, reactive element 26, and resonating reactive element 52 does not correspond to the frequency of the output signal 14. This may be important when medium and high power cauterisation is required because the sinusoidal generator output 14 is a higher voltage for medium and high power cauterisation than for low power cauterisation. Higher voltage at output 14 means that the magnification produced by the circuit network 16 is too great, therefore the value of resonating reactive element 52 is changed so that the circuit network 16 is no longer at resonance, thus reducing the amount of voltage magnification produced by the circuit network 16. The value of resonating reactive element 52 is changed by using the switch selector. Thus, medium and high power cauterising can be controlled using the circuit network 16. The reactive element 26 may be supplemented by one or more discrete capacitors. These capacitors may be used to tune the circuit network when it is not in resonance, that is when one of the different reactive elements is in use in the circuit network 16.

In other embodiments the actuator device 40 may be controlled automatically.

What is claimed is:

1. Apparatus for generating an ionised gas plasma flame for use in medicine, particularly for cauterisation comprising:

an electrical power source providing alternating voltage at a fixed frequency in the low Kilohertz region and with a magnitude below 100V;

circuit means having an output connected to the electrical power source;

a single insulated electrical conductor leading from the output and terminating with an electrically insulating free tip;

an end piece terminating the conduit means and surrounding the insulation-free tip of the conductor;

wherein the end-piece at its free end defines a nozzle through which the gas-flow can emerge, characterized in that the circuit means comprises a resonant circuit which is approximately resonant at the fixed frequency of the source and the resonant circuit includes an inductance to limit plasma current flow, the resonant circuit being arranged to provide an increasing voltage until a peak voltage is reached for initiating plasma discharge from the gas flow to form a plasma.

2. Apparatus according to claim 1, wherein a voltage detector continuously monitors the voltage at the tip and reduces the amplitude of the output voltage from the power source when the voltage at the tip is above a predetermined value.

3. Apparatus according to claim 1 wherein the circuit means includes a step-up transformer.

4. Apparatus according to claim 1, where the power source operates as a fixed frequency in the range 30–90 Khz and at a voltage in the range 2 to 50 V with a power level less than 30 watts.

5. Apparatus according to claim 1, where the gas is selected from the gases He, Ar, Ne, $H_2$, or $N_2$ or a combination thereof.

6. The apparatus according to claim 1, wherein the end piece has a blade.

7. The apparatus according to claim 6, wherein the blade is curved with a pointed end and is connected to electrical earth by earth wire.

8. The apparatus according to claim 1, wherein the end piece is angled partway along its length, wherein the electrically insulating free tip is shaped as a tube, and wherein the tube has a pointed end from which discharge initiates.

9. The apparatus according to claim 1, wherein the end piece is tubular.

10. The apparatus according to claim 1, wherein the plasma current flows to impart energy to the plasma only after the voltage increases and reaches the peak voltage for plasma initiation.

11. The apparatus according to claim 1, wherein power is delivered to the plasma at very low levels to impart energy to the plasma only after the voltage increases and reaches the peak voltage for plasma initiation.

12. The apparatus according to claim 1, wherein after the initiation of the plasma, the voltage falls to a level below the peak voltage required to initiate plasma discharge.

13. The apparatus according to claim 1, wherein the current in the circuit is an alternating current and is generated only when the plasma is initiated, so the current in the circuit is only generated for two short periods per cycle and the plasma is self-sustaining between these cycles.

14. The apparatus according to claim 1, wherein the circuit means comprises a resonating reactive element means which is selected to achieve resonance at a fixed frequency of the power source and a limiting element means to limit the voltage peak to a level required to initiate discharge of the plasma and to reduce the sharpness of resonant peaks produced by the resonating reactive element means.

15. The apparatus according to claim 14, wherein the circuit means further comprises a transformer means to increase the voltage from the circuit means to provide a voltage for plasma initiation and a detector means connected to the transformer that automatically reduces the amplitude of the voltage from the generator to reduce the voltage at the transformer to a predetermined value.

16. The apparatus according to claim 1, further comprising a gas source means used to supply a substantially inert gas which is ignited to form an ionized plasma flame, an actuator means which allows easy operator adjustment of the gas flow and electrical power and a controller means to control the power source and the gas source and is responsive to the actuator.

17. The apparatus according to claim 16, wherein the circuit means comprises a resonating reactive element means which is selected to achieve resonance at a fixed frequency of the power source and a limiting element means to limit the voltage peak to a level required to initiate discharge of the plasma and reduce the sharpness of resonant peaks produced by the resonating reactive element means, a transformer means to increase the voltage from the circuit means to provide a voltage for plasma initiation and a detector means connected to the transformer that automatically reduces the amplitude of the voltage from the generator to reduce the voltage at the transformer to a predetermined value.

* * * * *